United States Patent
Langella et al.

(10) Patent No.: US 10,441,524 B2
(45) Date of Patent: Oct. 15, 2019

(54) COSMETIC AND HOUSEHOLD CARE COMPOSITION

(71) Applicant: LAMBERTI SPA, Albizzate (IT)

(72) Inventors: Valentina Langella, Milan (IT); Mauro Riccaboni, Legnano (IT); Barbara Biasotti, Casarza Ligure (IT); Chiara Fumagalli, Besnate (IT); Giovanni Floridi, Novara (IT); Giuseppe Li Bassi, Gavirate (IT)

(73) Assignee: Lamberti SPA, Albizzate (VA) (IT)

( * ) Notice: Subject to any disclaimer, the term of this patent is extended or adjusted under 35 U.S.C. 154(b) by 0 days.

(21) Appl. No.: 14/916,873

(22) PCT Filed: Nov. 20, 2013

(86) PCT No.: PCT/EP2013/074279
§ 371 (c)(1),
(2) Date: Mar. 4, 2016

(87) PCT Pub. No.: WO2014/027120
PCT Pub. Date: Feb. 20, 2014

(65) Prior Publication Data
US 2016/0193134 A1    Jul. 7, 2016

(30) Foreign Application Priority Data
Sep. 4, 2013   (IT) .............. VA2013A0048

(51) Int. Cl.
| A61K 8/73 | (2006.01) |
|---|---|
| A61Q 5/02 | (2006.01) |
| A61Q 5/12 | (2006.01) |
| A61K 8/19 | (2006.01) |
| A61K 8/41 | (2006.01) |
| A61Q 19/10 | (2006.01) |

(52) U.S. Cl.
CPC ............... *A61K 8/737* (2013.01); *A61K 8/19* (2013.01); *A61K 8/416* (2013.01); *A61K 8/73* (2013.01); *A61Q 5/02* (2013.01); *A61Q 5/12* (2013.01); *A61Q 19/10* (2013.01); *A61K 2800/30* (2013.01); *A61K 2800/48* (2013.01); *A61K 2800/5426* (2013.01)

(58) Field of Classification Search
CPC .......... A61K 8/737; A61K 8/19; A61K 8/416; A61K 8/73; A61K 2800/30; A61K 2800/48; A61K 2800/5426; A61Q 5/02; A61Q 5/12; A61Q 19/10
See application file for complete search history.

(56) References Cited

U.S. PATENT DOCUMENTS

| 3,589,978 A  * | 6/1971 | Kamal ................... D21H 17/08 162/158 |
|---|---|---|
| 4,031,307 A | 6/1977 | Demartino et al. |
| 4,061,602 A | 12/1977 | Oberstar et al. |
| 4,753,659 A | 6/1988 | Bayerlein et al. |
| 5,733,854 A | 3/1998 | Chowdhary et al. |
| 7,262,157 B2 | 8/2007 | Utz et al. |
| 7,759,296 B2 | 7/2010 | Lepilleur et al. |
| 2001/0051140 A1 | 12/2001 | Wielinga et al. |
| 2001/0051143 A1 * | 12/2001 | Cottrell ................... A61K 8/737 424/70.28 |

FOREIGN PATENT DOCUMENTS

| CA | 2023324 A1 | 1/1992 | |
|---|---|---|---|
| EP | 323627 A2 | 7/1989 | |
| EP | 1630176 A1 | 3/2006 | |
| EP | 1739095 A1 | 1/2007 | |
| EP | 1786840 A1 | 5/2007 | |
| EP | 2089435 A1 | 8/2009 | |
| FR | 2513265 A1 | 3/1983 | |
| WO | 2001097761 A1 | 12/2001 | |
| WO | WO2008/058768 | * 5/2008 | ............. C08B 37/14 |
| WO | WO2012/054278 | * 4/2012 | ............... A61K 8/81 |

OTHER PUBLICATIONS

R.J. Chudzikowski, Guar Gum and its Applications, 22 J Soc. Cosmet. Chem. 43 (1971).*

Whistler, R. et al., "Industrial Gums: Polysaccharides and their Derivatives," Third Ed., Chapter Eight (8), Academic Press (1993).

* cited by examiner

*Primary Examiner* — Sean M Basquill
(74) *Attorney, Agent, or Firm* — Vorys, Sater, Seymour and Pease LLP; Elisabeth Rather Healey

(57) ABSTRACT

Personal care and household care compositions comprising a conditioner and rheology modifier based on a cationic galactomannan or cationic xyloglucan having cationic degree of substitution comprised between 0.01 and 3, free from (3-chloro-2-hydroxypropyl)trimethyl ammonium chloride and free from (2,3-epoxypropyl)trimethyl ammonium chloride.

6 Claims, No Drawings

COSMETIC AND HOUSEHOLD CARE COMPOSITION

The present invention relates to personal care compositions and to household care compositions comprising a cationic galactomannan or a cationic xyloglucan having cationic degree of substitution comprised between 0.01 and 3, free from (3-chloro-2-hydroxypropyl)trimethyl ammonium chloride and free from (2,3-epoxypropyl)trimethyl ammonium chloride.

The procedure for the preparation of the cationic galactomannan or xyloglucan comprises the reaction of a galactomannan or xyloglucan with (3-chloro-2-hydroxypropyl)trimethyl ammonium chloride or (2,3-epoxypropyl)trimethyl ammonium chloride and a subsequent step in which the unreacted cationizing agent, which is known to create toxicological concern, is converted into the non noxious, beneficial cosmetically accepted ingredient (2,3-dihydroxypropyl)trimethyl ammonium chloride.

This procedure provides a conditioner and rheology modifier comprising i) from 60 to 90% by weight of a cationic galactomannan, or a cationic xyloglucan, having cationic degree of substitution between 0.01 and 3, ii) from 1% to 10% by weight of (2,3-dihydroxypropyl)trimethyl ammonium chloride and iii) less than 0.15% by weight of (3-chloro-2-hydroxypropyl)trimethyl ammonium chloride.

FIELD OF THE INVENTION

Cationic polysaccharides are derivatives of natural origins that are commonly used as industrial additives, due to their conditioning property (i.e. they improve the sensorial characteristics of the substrate to which they are applied on, generally paper, skin, hair or fabric).

This characteristic renders them industrially useful for the preparation of shampoos and hair conditioners, creams and detergents for personal or household care and for softeners conferring a soft touch and antistatic properties to fabrics (see as an example "Conditioning Agents for Hair & Skin", Ed. R. Schueller and P. Romanowski, Marcel Dekker Inc, NY, 1999). Beside their conditioning power, the capability of these polysaccharides to thicken and regulate the rheology of the solutions in which they are dissolved is also industrially useful. In particular, among cationic polysaccharides, the cationic derivatives of guar gum and cassia gum (which are both galactomannan) have shown optimal results in improving the wet and dry combability of hair washed with shampoo formulated therewith.

During the last few years, particular attention has been placed to the toxicity of the raw materials used for the fabrication of cosmetic products. The EU Regulation 1223/2009 that substituted the EC Directive 76/768/EEC since Jul. 11, 2013, limits or prohibits the presence of certain substances as cosmetic ingredients, with the aim to safeguard the consumer health.

In particular, the above cited Regulation in Article 15 prohibits the use of the substances classified as CMR of category 1A, 1B or 2 under Part 3 of Annex VI to Regulation (EC) Nr. 1272/2008 in cosmetic products.

The synthesis of industrially useful cationic derivatives of polysaccharides, generally requires the reaction of (2,3-epoxypropyl)trimethyl ammonium chloride or (3-chloro-2-hydroxypropyl)trimethyl ammonium chloride in presence of alkaline catalysts (such as sodium hydroxide) with the hydroxyl groups of the polysaccharide. The reaction is generally performed in the presence of water or water/solvent(s) mixtures, with yields ranging from 40% to 90%, resulting in a mixture of cationic polysaccharide, unreacted cationising agent and some (2,3-dihydroxypropyl)trimethyl ammonium chloride coming from the hydrolysis of the cationising agent.

The reagent (2,3-epoxypropyl)trimethyl ammonium chloride is classified as a carcinogenic substance CMR 1B; the reagent (3-chloro-2-hydroxypropyl)trimethyl ammonium chloride, even if less toxic than the corresponding epoxide, is classified as CMR 2.

Residues of unreacted reagent are therefore to be avoided and the cationic polysaccharides for the use in cosmetic formulations or in formulations that come to direct contact with the skin, such as household care compositions, are generally purified, usually with water and/or solvents, to remove the reaction by-products and the residues of unreacted raw materials. This purification increases the production costs and has several technological problems connected with the necessity of adding a further step to the synthesis and of managing a lot of waste water and/or recycling the solvent. There is still therefore the need to provide a cationic polysaccharide which is devoid of toxic unreacted reagents and does not necessitate further purification steps.

STATE OF THE ART

Cationic guar derivatives are known since the early '70s, when their use is cited in the production of waterproof paper (U.S. Pat. No. 3,589,978); cationic cassia derivatives for industrial uses were prepared in the early '80s (FR 2513265).

The first uses of cationic guar derivatives in cosmetics go back to 1977, when a cationic derivative of guar was used in the preparation of a so-called "two in one" shampoo, having hair conditioning characteristics beside the normal detergent power (U.S. Pat. No. 4,061,602).

The cationic derivatives of galactomannans used in cosmetic are known for example with the INCI names of: Hydroxypropyl Guar Hydroxypropyltrimonium Chloride (chemically, it is guar gum, 2-hydroxypropyl 2-hydroxy-3-(trimethylammonio)propyl ether chloride); Guar Hydroxypropyltrimonium Chloride (chemically, it is guar gum, 2-hydroxy-3-(trimethylammonio)propyl ether, chloride); *Caesalpinia Spinosa* Hydroxypropyltrimonium Chloride (chemically, it is tara gum, 2-hydroxy-3-(trimethylammonio)propyl ether, chloride); Cassia Hydroxypropyltrimonium Chloride; Locust Bean Hydroxypropyltrimonium Chloride; *Trigonella Foenum*-Graecum Hydroxypropyltrimonium Chloride. Most patent publications describing the synthesis of the above cited cationic derivatives, either ignore the possible presence of impurities in the final product or suggest to eliminate them by washing with water and/or solvents.

According to what is described in U.S. Pat. No. 3,589,978, the cationization reaction can be carried out in a solvent such as isopropanol, methanol, ethanol and tert-butanol; in the Example A of the same patent, at the end of the reaction and after neutralisation of the alkali excess, the product is dried, milled and washed with methanol, which is itself a toxic product, in the attempt to eliminate the un-reacted quaternary reagent.

In U.S. Pat. No. 4,031,307 the preparation of cationic derivatives of guar in a biphasic system is described; after the reaction, the obtained product is separated by centrifugation or filtration and preferably purified by means of a first washing step with the water-solvent mixture used in synthesis, and with a second washing step with a more anhydrous form of the same solvent.

In US 2001/0051143, the preparation of cationic guar derivatives comprises at the end of the reaction a first washing step with 85% by weight aqueous isopropanol and a second washing step with pure isopropanol; in US 2001/0051140 the preparation of guar cationic derivatives comprising, at the end of the reaction, two washings steps with 85% wt aqueous isopropanolis described.

Cassia cationic derivatives for home and personal care application are reported for example in U.S. Pat. Nos. 7,262,157 and 7,759,296.

For their synthesis, the functionalization method according to U.S. Pat. Nos. 4,753,659 and 5,733,854 is cited; in these patents nothing is said about the presence of impurities deriving from the cationizing reagents.

In U.S. Pat. No. 7,759,296 the detailed preparation of cationic cassia for hair fixative application is reported in Example 1; after the reaction with (2,3-epoxypropyl)trimethyl ammonium chloride the product is washed with isopropanol.

EP 1739095 and EP 1630176 disclose the preparation of cationic derivatives of galactomannans from Tara gum (from seeds of *Caesalpinia spinosa*), Locust Bean gum (from seeds of *Ceratonia siliqua*) and Fenugreek gum (from seeds of *Trigonelle foenum-graecum*, and their use in personal care application. Again, nothing is said about the presence of impurities and in the examples the cationic derivatives after the preparation were dissolved and then precipitated using methanol.

In EP 2089435 the elimination of the toxic reagent from the reaction mixture is performed by means of water/solvent washes.

None of the above cited patent publications describes a step in which the residual cationizing agent is converted into a cosmetically acceptable ingredient.

Many cationic guar derivatives which are currently on the market, are purified by crosslinking with borates and washing them with water only, as described for example in CA 2,023,324; the so obtained cationic guar derivatives contain small amounts of boron (borated guars).

The aim of the cross-linking with boric acid or any other cross-linker is to form bonds between the polysaccharides chains, that render the product insoluble in water and thus washable.

As an alternative to borax, other cross-linkers such as glyoxal and titanium salts have been developed.

Unfortunately, all these purification procedures involve large quantities of water and solvents, and in some cases, the use of toxic substances such as borax derivatives.

Moreover it is really difficult, almost impossible, to industrially purify by washing cationic polysaccharides with high degree of substitution, for example higher than 0.4, or cationic derivatives that have been depolymerised, because of their relatively higher solubility.

The Applicant has now found a process for the preparation of cationic galactomannans and xyloglucans that comprises a second further alkaline treatment, which takes place after the reaction with (3-chloro-2-hydroxypropyl)trimethyl ammonium chloride, or with (2,3-epoxypropyl)trimethyl ammonium chloride, and converts the unreacted residual reagents into the non noxious, beneficial, cosmetically accepted ingredient (2,3-dihydroxypropyl)trimethyl ammonium chloride.

The alkaline post-treatment permits to avoid washing steps and produces cationic galactomannans and xyloglucans that are soluble at all pHs and free from toxic contaminants that would compromise the toxicological characteristics of the cosmetic formulations in which they are used as an ingredient.

Moreover, despite what is reported in the literature, for example in Starch/Stärke 33 (1981) Nr. 9, S. 310-312, the addition of a second alkali treatment after the cationization, does not affect negatively the reaction efficiency and the cationic degree of substitution, that remain at the highest level.

In a preferred embodiment of this invention it is also possible to use the alkaline post-treatment to diminish the viscosity of the final product, without the need of adding a further depolymerization step.

A process for the preparation of cationic guar which includes a step of purification with an alkali after synthesis has been generically described in WO 2001/097761. According to this patent application the amount of alkali which is totally used in the whole process can vary from about 10 to 100% by weight, based on the weight of the galactomannan.

Nothing more is said about this post-derivatization treatment, how much and when the alkali is added, the treatment conditions and the influence of this treatment on the impurities, on the degree of substitution and on the final viscosity of the cationic guar. Moreover, in Example I, after the sodium hydroxide treatment and subsequent neutralization, the cationic guar is purified by solvent washings as usual.

With the expressions "cationic galactomannan" or "cationic xyloglucan" in the present text we mean the chlorides of the 2-hydroxy-3-(trimethylammonio)propyl ether of a galactomannan or of a xyloglucan, (which are also known as the chlorides of the 2-hydroxy-3-(trimethylammonium)propyl ether of the galactomannan or xyloglucan), that possibly bear other substituents.

In the present text, with the expression "cationic degree of substitution", ($DS_{cat}$) we mean the average number of hydroxyl groups substituted with a cationic group on each anhydroglycosidic unit of the polysaccharide determined by means of $^1$H-NMR.

With the expression "hydroxyalkyl molar substitution" (MS), we mean the average number of hydroxyalkyl substituents on each anhydroglycosidic unit of the polysaccharide measured by means of $^1$H-NMR.

With the expression "hydrophobic degree of substitution" ($DS_H$), we mean average number of hydrophobic substituents on each anhydroglycosidic unit of the polysaccharide measured by means of gas-chromatography.

With the expression "carboxyalkyl degree of substitution" ($DS_{AN}$), we mean the average number of hydroxyl groups substituted with a carboxyalkyl group on each anhydroglycosidic unit of the polysaccharide measured by means of titration.

With the expressions "cosmetic compositions" or "personal care compositions" we mean the compositions normally used for personal care, such as hair care products, skin care products and oral care compositions.

DESCRIPTION OF THE INVENTION

It is therefore a fundamental object of the present invention a personal care composition and a household care composition comprising a cationic galactomannan or cationic xyloglucan having cationic degree of substitution comprised between 0.01 and 3 which is prepared with the following procedure: a) 100 parts by weight of galactomannan or xyloglucan are reacted with from 1 to 600 parts by weight of (3-chloro-2-hydroxypropyl)trimethyl ammonium chloride or of (2,3-epoxypropyl)trimethyl ammonium chloride and with from 0.4 to 200 parts by weight of sodium hydroxide (or equivalent amount of another alkaline hydroxide) in from 5 to 500 parts of water or of a water/alcohol mixture containing from 20 to 100% by weight of water; b) from 0.1 to 400 parts by weight of sodium hydroxide (or equivalent amount of another alkaline hydroxide) are added to the obtained mixture and the mixture is stirred for from 10 to 300 minutes, preferably from 60 to 150 minutes, at temperature comprised between 30° C. and 90° C., preferably between 45° C. and 80° C.; c) optionally the pH of the mixture is corrected with an acid; d) the mixture obtained from step b) or c) is directly dried and milled.

Another object of the present invention is a procedure for the preparation of a cationic galactomannan or a cationic xyloglucan having cationic degree of substitution comprised between 0.01 and 3 comprising the following steps: a) 100 parts by weight of galactomannan or xyloglucan are reacted with from 1 to 600 parts by weight of (3-chloro-2-hydroxypropyl)trimethyl ammonium chloride or of (2,3-epoxypropyl) trimethyl ammonium chloride and with from 0.4 to 200 parts by weight of sodium hydroxide (or equivalent amount of another alkaline hydroxide) in from 5 to 500 parts of water or of a water/alcohol mixture containing from 20 to 100% by weight of water; b) from 0.1 to 400 parts by weight of sodium hydroxide (or equivalent amount of another alkaline hydroxide) are added to the obtained mixture and the mixture is stirred for from 10 to 300 minutes, preferably from 60 to 150 minutes, at a temperature comprised between 30° C. and 90° C., preferably between 45° C. and 80° C.; c) optionally the pH of the mixture is corrected with an acid; d) the mixture obtained from step b) or c) is directly dried and milled.

The above described procedure for the preparation of a cationic galactomannan or a cationic xyloglucan provides a conditioner and rheology modifier, useful as ingredient of personal care compositions and household care compositions, comprising i) from 60 to 90% by weight of a cationic galactomannan, or a cationic xyloglucan, having cationic degree of substitution between 0.01 and 3, preferably between 0.05 and 0.7 ii) from 1% to 10% by weight of (2,3-dihydroxypropyl)trimethyl ammonium chloride and iii) less than 0.15% by weight of (3-chloro-2-hydroxypropyl) trimethyl ammonium chloride, which is a further object of the present invention.

Still further objects of the present invention are personal care compositions and household care compositions, preferably personal care compositions, comprising the above described conditioner and rheology modifier.

DETAILED DESCRIPTION OF THE INVENTION

According to a preferred embodiment of the present invention, in step a) of the procedure for the preparation of the cationic galactomannan or xyloglucan, from 1 to 600 parts by weight of (3-chloro-2-hydroxypropyl)trimethyl ammonium chloride and from 0.4 to 200 parts by weight of sodium hydroxide are added; more preferably, in step a) of the procedure from 10 to 180 parts by weight of (3-chloro-2-hydroxypropyl)trimethyl ammonium chloride and from 3 to 60 parts by weight of sodium hydroxide are added, thus obtaining at the end of the preparation a cationic galactomannan or xyloglucan having a DS comprised between 0.05 and 0.7.

The above procedure is particularly suitable for the preparation of cationic galactomannans or xyloglucans with $DS_{cat}$ comprised between 0.4 and 0.7, whose purification would be difficult with the washing methods of the prior art.

The alcohol useful for the procedure of the invention is preferably ethanol, isopropanol, or mixtures thereof.

Preferably in step a) of the procedure from 50 to 200 parts by weight of water or of water/alcohol mixture each 100 parts by weight of galactomannan or xyloglucan are used.

Preferably, in step a), the galactomannan or xyloglucan, the alkaline hydroxide and the cationizing agent (3-chloro-2-hydroxypropyl)trimethyl ammonium chloride or (2,3-epoxypropyl)trimethyl ammonium chloride are reacted for about 1 to 4 hours at temperature from about 40° C. to about 80° C., before step b) takes place. Most preferably, the alkaline hydroxide is added to the galactomannan or xyloglucan that has been pre-mixed with the water or with the water/solvent mixture and stirred for about 15 to 45 minutes; subsequently, the cationizing agent is added and reacted at about 40° C. to 70° C. for about 1 to 3 hours, before step b) takes place.

The galactomannans useful for the preparation of the cationic derivatives of the invention include all polysaccharides which are made of galactose and mannose units and may have in addition, small amounts of other types of sugar units.

They occur mainly in the endosperm of seeds of various legumes, such as *Cyamopsis tetragonolobus* (Guar), *Ceratonia siliqua* (Locust bean or Carob), *Caesalpinia spinosa* (Tara), *Cassia occidentalis* (Cassia), *Sesbania* and *Trigonella foenum-graecum* (Fenugreek).

In particular, the galactomannans consist of a main chain of mannose units linked together by 1-4-β-glycosidic linkages from which galactose units branch by means of 1-6-α-glycosidic linkages. The ratio of mannose units to galactose units can vary from one source to another. In order of increasing ratio, fenugreek gum has a mannose to galactose ratio about 1:1, sesbania gum about 1.6:1, guar gum about 2:1, tara gum about 3:1, locust bean gum or carob gum about 4:1 and cassia gum about 5:1.

The best known galactomannans are those from *Cyamopsis tetragonoloba* L. (guar), *Cesalpinia spinosa* L. (tara), and *Ceratonia siliqua* L. (locust bean). Unsubstituted mannans are completely insoluble in water, The attachment of galactose units to the primary hydroxyl groups of the mannose units (C-6 atom of the mannose molecule) by 1,6-α-glycosidic bonds increases water solubility, particularly cold water solubility.

The cationic galactomannans described herein can be prepared using the gum in the form of flour (powder) or in the form of "splits".

Splits are obtained by mechanical separation of the endosperm from the hull and germ of the seed in as pure and intact form as possible with no other processing steps. These splits contain, as impurities in percentage varying from species to species, from about 6 to 12 percent moisture, from 2 to 7 percent proteins and from 2 to 7 percent acid insoluble residue.

The flour usually have a particle size range of from about 4 to about 400 mesh (ASTM Standard Sieve Series).

The galactomannan suitable for obtaining the cationic derivative of the invention has preferably a Brookfield® RVT viscosity, measured at 25° C. and 20 rpm on a 1.0% by weight water solution, comprised between 50 and 10,000 mPa·s and a weight average molecular weight ($M_w$) typically of between 50,000 and 3,000,000 Dalton.

In a preferred embodiment, the personal care composition and the household care composition comprise a cationic galactomannan prepared by the above described procedure. In the most preferred embodiment, the cationic galactomannan is guar gum.

Xyloglucans are hemicellulose that occur in the primary cell wall of all vascular plants. A typical example of xyloglucan useful for the realization of the invention is tamarind gum.

Tamarind (*Tamarindus Indica*) is a leguminous evergreen tall tree produced in the tropics. Tamarind gum (tamarind powder or tamarind kernel powder) is obtained by extracting and purifying the powder obtained by grinding the seeds of tamarind.

Its backbone consists of D-glucose units joined with (1-4)-β-linkages similar to that of cellulose, with a side chain of single xylose unit attached to every second, third and fourth of D-glucose unit through α-D-(1-6) linkage. One galactose unit is attached to one of the xylose units through β-D-(1-2) linkage. The molar ratio between glucose, galactose and xylose is about 3:1:2.

The xyloglucan gum suitable for obtaining the cationic derivative of the invention has preferably a Brookfield® RVT viscosity, measured at 25° C. and 20 rpm on a 1.0% by weight water solution, comprised between 50 and 10,000 mPa·s and a weight average molecular weight ($M_w$) typically of between 100,000 and 1,000,000 Dalton.

The procedure of the invention can comprise one or more further derivatization steps, for example hydroxyalkylation, carboxyalkylation, hydrophobization steps, or combination thereof.

In this case, the cationic galactomannan and xyloglucan of the invention may also contain further substituent groups such as hydroxyalkyl substituents, wherein the alkyl represents a straight or branched hydrocarbon moiety having 1 to 5 carbon atoms (e.g., hydroxyethyl, or hydroxypropyl, hydroxybutyl), hydrophobic substituents, carboxyalkyl substituents, or combinations thereof.

The process for introducing a hydroxyalkyl substituent on a polysaccharide is well known in the art.

Typically, the hydroxyalkylation of a polysaccharide is obtained by the reaction with reagents such as alkylene oxides, e.g. ethylene oxide, propylene oxide, butylene oxide and the like, to obtain hydroxyethyl groups, hydroxypropyl groups, or hydroxybutyl groups, etc.

The resulting hydroxyalkyl cationic galactomannan and xyloglucan may have a MS comprised between 0.1 and 3.0, preferably between 0.1 and 2.0, more preferably between 0.1 and 1.5.

The hydrophobization of the cationic galactomannan and xyloglucan of the invention is obtained by the introduction of hydrophobic groups.

The introduction of hydrophobic groups on galactomannans is described for example in EP 323627 and EP 1786840. The same methods may be used on xyloglucans.

Typical derivatizing agents bringing a hydrophobic group include linear or branched $C_2$-$C_{24}$ alkyl and alkenyl halides, linear or branched alkyl and alkenyl epoxides containing a $C_6$-$C_{24}$ hydrocarbon group and alkyl and alkenyl glycidyl ethers containing a $C_4$-$C_{24}$ linear or branched hydrocarbon group.

A suitable glycidyl ether hydrophobizing agent can be, for example, butyl glycidyl ether, t-butyl glycidyl ether, 2-ethylhexyl glycidyl ether, dodecyl glycidyl ether, hexadecyl glycidyl ether, behenyl glycidyl ether and nonylphenyl glycidyl ether.

Representative alkyl epoxides include, but are not limited to, 1,2-epoxy hexane, 1,2-epoxy octane, 1,2-epoxy decane, 1,2-epoxy dodecane, 1,2-epoxy tetradecane, 1,2-epoxy hexadecane, 1,2-epoxy octadecane and 1,2-epoxy eicosane.

Exemplary halide hydrophobizing agents include, but are not limited to, ethyl, propyl, isopropyl, n-butyl, t-butyl, pentyl, neopentyl, hexyl, octyl, decyl, dodecyl, myristyl, hexadecyl, stearyl and behenyl bromides, chlorides, and iodides.

Other derivatizing agents suitable for introducing the hydrophobic modification include alkyl- and alkenyl-β-hydroxy-γ-chloropropyl ethers and epoxy derivatives of triglycerides.

In a preferred embodiment of the invention, the cationic substituent is 2-hydroxy-3-(trimethylammonio)propyl ether chloride and the hydrophobic substituent contains a linear alkyl or alkenyl chain containing between 6 and 24 carbon atoms or a mixture of such alkyls or alkenyls.

The hydrophobically modified cationic galactomannan or xyloglucan of the invention may have hydrophobic degree of substitution ($DS_H$) of from $1 \cdot 10^{-5}$ to $5 \cdot 10^{-1}$, preferably from $1 \cdot 10^{-4}$ to $1 \cdot 10^{-1}$.

In a further particular embodiment, the cationic galactomannan and xyloglucan of the invention may contain both hydroxyalkyl substituents and hydrophobic substituents. In this case the MS is comprised between 0.1 and 3.0 and the $DS_H$ between $1 \cdot 10^{-5}$ and $5 \cdot 10^{-1}$.

In another embodiment, the cationic galactomannan and xyloglucan of the invention are carboxyalkylated. The carboxyalkyl cationic polysaccharides of the invention have a degree of carboxyalkyl substitution ($DS_{AN}$) ranging from 0.01 to 1.0.

Halo-carboxylic acids or their salts may be used for the preparation of carboxyalkyl cationic galactomannans and xyloglucans. The preferred halo-carboxylic acid is chloroacetic acid.

In a more preferred embodiment, the cationic galactomannan and xyloglucan contain only cationic substituents and have a $DS_{cat}$ comprised between 0.05 and 0.7, most preferably between 0.4 and 0.7.

Further details about the preparation of the cationic galactomannans and xyloglucans suitable for the realization of the present invention can be found in the literature, for example in "Industrial Gums: Polysaccharides and their Derivatives", 3rd Ed., Whistler, Roy L., and BeMiller, James N., Academic Press (1993).

The derivatization reactions (cationization, carboxyalkylation, hydroxyalkylation, hydrophobization) can follow any order.

By way of example, when the cationic galactomannan and xyloglucan of the invention also contain hydroxyalkyl substituents, the latter may be introduced in the last step, after the cationization step a) and the, optional, hydrophobization have occurred.

The characterizing step of the procedure of the invention is step b).

Step b) can be performed at any time after the cationization of the polysaccharides, but preferably it is performed after all the derivatization reactions have been carried out.

In a preferred embodiment of the invention, from 1 to 180 parts by weight, more preferably from 2 to 90 parts by weight, of sodium hydroxide (or equivalent amount of other alkaline hydroxide) each 100 parts of galactomannan or xyloglucan are added in step b).

After step b), the pH of cationic polysaccharide can opportunely be adjusted. Any acid may be selected to adjust the pH of the reaction mixture, including strong acids such as hydrochloric acid and sulfuric acid or weak acids such as acetic acid, lactic acid, citric acid, carbon dioxide and fumaric acid. In preferred embodiments acetic acid or fumaric acid are used. In another preferred embodiment, the pH of the reaction mixture obtained after step b) is lowered by addition of carbon dioxide. The amount of acid used is the amount which is necessary to reach the desired pH value, which is usually from 4 to 11.

The procedure of the invention can comprise further treatments with several known reagents and methods, for example: acids; biochemical oxidants, such as galactose-oxidase, mannanase or other enzymes; chemical oxidants, such as hydrogen peroxide; physical methods, such as high speed agitation, shearing machines, thermal methods; combinations of these reagents and methods. Reagents such as sodium metabisulfite or inorganic salts of bisulfite may also be optionally included.

A light crosslinking of the galactomannan or xyloglucan (for example with borax, glyoxal, titanium or aluminium salts), to obtain dispersibility of the cationic polysaccharides and delayed solubilisation, can also be performed.

All the above further treatments can be also performed on the galactomannan and the xyloglucan before step a) or soon after step b).

In another embodiment, the cationic galactomannan and xyloglucan are depolymerized by known methods, such as oxidation, for example with alkali or hydrogen peroxide, or by other depolymerization reactions, such as enzymatic or thermal depolymerisation, or acid hydrolysis. The depolymerized cationic galactomannan or xyloglucan used in this invention are preferably prepared by treatments with alkali.

In a preferred embodiment, the depolymerized cationic galactomannan and xyloglucan of the invention is prepared by reducing the molecular weight of the galactomannan or xyloglucan before any derivatization. Depolymerization can be performed using the already mentioned methods.

At the end of the preparation procedure, the cationic galactomannan or xyloglucan are dried and recovered using means known in the art. Examples of such means include air drying, fluidized bed drying, filtering, centrifuging, addition of solvents, freeze drying and the like. The use of fluidized bed drying is particularly recommended.

According to the innovative aspect of the invention no purification by washing with water or solvents is contemplated in the disclosed procedure that provides the conditioner and rheologly modifier which is a further object of the present invention.

The conditioner and rheology modifier comprises i) from about 60 to about 90% by weight, preferably from about 70 to about 85% by weight, of the cationic galactomannan or cationic xyloglucan having cationic degree of substitution between 0.01 and 3, preferably between 0.05 and 0.7, more preferably between 0.4 and 0.7, ii) from 1% to 10% by weight, more preferably from 2.5% to 8% by weight, of (2,3-dihydroxypropyl)trimethyl ammonium chloride and iii) less than 0.15% by weight, more preferably less than 0.05% by weight, of (3-chloro-2-hydroxypropyl)trimethyl ammonium chloride.

The conditioner and rheology modifier may further contain some residual water, normally between 1 and 10% by weight of water; further minor amounts of non-noxious by-products deriving from the other additional derivatizing reactions, such as glycols and polyglycols deriving from propylene oxide, may also be present, normally in amount between 0 to 15% by weight.

Other ingredients that may present are salts deriving from the alkaline hydroxide and possibly from the acid which is added to adjust the pH, normally in amount between 1 and 15% by weight.

The conditioner and rheology modifier has an ash content from 2 to 15% by weight (determined at 650° C.), usually from 8 to 15%.

Surprisingly it has been found that, at least in typical skin and hair cleaning formulations, the conditioner and rheology modifier of the invention provides a thickening performance which is higher than the one which is expected on the base of its active polysaccharide content (which of course is lower than that of analogue purified cationic galactomannan or xyloglucan).

The cationic galactomannan of the conditioner and rheology modifier has a weight average molecular weight ($M_w$) between 50,000 and 2,000,000; the cationic xyloglucan has a weight average molecular weight ($M_w$) typically of between 100,000 and 1,000,000 Dalton.

The conditioner and rheology modifiers have RVT Brookfield viscosity of from 15 to 5000, preferably from 30 to 3000, at 1% by weight in water, 20 rpm and 20° C.

In case the cationic galactomannans or xyloglucans are depolymerized, they have RVT Brookfield® viscosity at 1% by weight in water, 20° C., 20 rpm from 15 to 800 mPa·s, preferably from 30 to 500 mPa·s.

According to a particularly advantageous aspect of the invention, the treatment with the alkali of step b) permits to eliminate the toxic impurities coming from the cationizing reagent without the need of any further purification by washing and to obtain a conditioner and rheology modifier useful for personal care and household care applications.

The conditioner and rheology modifier and the cationic galactomannan or xyloglucane of the invention are free from toxic solvents, from (3-chloro-2-hydroxypropyl)trimethyl ammonium chloride and from (2,3-epoxypropyl)trimethyl ammonium chloride. Moreover, the conditioner and rheology modifier contains from 1% to 10% by weight of (2,3-dihydroxypropyl)trimethyl ammonium chloride, formed from the reaction of (3-chloro-2-hydroxypropyl) trimethyl ammonium chloride or of (2,3-epoxypropyl)trimethyl ammonium chloride, that is itself a cosmetic ingredient known with the INCI name of Dihydroxypropyl Trimonium Chloride.

A clear advantage of the procedure according the invention is that it allows to obtain the conditioner and rheology modifier with high yields, due to the fact that no purification by washing is necessary.

With the expression "free from (3-chloro-2-hydroxypropyl)trimethyl ammonium chloride", we mean that the residual concentration of (3-chloro-2-hydroxypropyl)trimethyl ammonium chloride is below 0.15 by weight. Preferably the conditioner and rheology modifier and the cationic galactomannan and xyloglucan of the invention contain less than 0.05% by weight, more preferably less than 0.01% by weight, of (3-chloro-2-hydroxypropyl)trimethyl ammonium chloride.

With the expression "free from (2,3-epoxypropyl)trimethyl ammonium chloride", we mean that the residual concentration of (2,3-epoxypropyl) trimethyl ammonium chloride is below 0.15% by weight. Preferably the conditioner and rheology modifier and the cationic galactomannan and xyloglucan contain less than 0.05% by weight, more preferably less than 0.01% by weight, of (2,3-epoxypropyl) trimethyl ammonium chloride.

Advantageously, the conditioner and rheology modifier and the cationic galactomannan or xyloglucan of the invention are also devoid of glyoxal, boron, or other crosslinking agents.

Glyoxal and boron compounds are often used in the preparation of cationic derivatives of polysaccharides to facilitate dissolution of the final product and/or to temporarily insolubilize the crude product and consent its purification by washing with water and/or solvent.

The cationic galactomannan and xyloglucan of the invention, do to need to be treated with glyoxal, boron compounds or other crosslinkers, because they dissolve without the formation of lumps under moderate to high sheer stirring, and do not need to be washed to get free from toxic by-products, as explained above.

The cationic galactomannan and cationic xyloglucan are therefore preferably uncrosslinked.

When low stirring capabilities are to be employed in the dissolution of the conditioner and rheology modifier, and the cationic galactomannan or cationic xyloglucan are uncrosslinked, to avoid the formation of lumps, it may be advisable to pre-disperse it in a suitable acceptable organic medium, such as glycerol, to form a slurry and to add the slurry to the personal care composition or household care compositions while gently mixing.

According to a particularly preferred embodiment, the conditioner and rheology modifier is devoid from glyoxal, boron, and crosslinking agents (such as titanium salts) and has $DS_{cat}$ comprised between 0.05 and 0.7, more preferably between 0.4 and 0.7. The conditioner and rheology modifier obtained by means of the procedure of the invention can be used as ingredients in the most different cosmetic and household care compositions, and especially in hair care compositions, where their capability of binding through their positive charges to substrates having weak negative charges, together with their capability to thicken and to regulate the rheology of water solutions, are exploited.

The combability of hair treated with a conditioner and rheology modifier according to the invention, based on a cationic galactomannan, in comparison with hair treated with a purified cationic galactomannan of the prior art was tested and, unexpectedly, the performance of the former resulted to be strikingly higher, thus giving evidence of its superior conditioning properties.

The conditioner and rheology modifiers of the invention show their conditioning and viscosifying characteristics also when dosed at rather low concentrations, for example at concentration around 0.3% by weight of the formulated cosmetic.

The conditioner and rheology modifiers and the cationic galactomannans and xyloglucans of the invention are also useful in other industrial fields, where the toxicity characteristics of the raw materials are of particular importance, such as for example in the paper industry.

They may be present in cosmetic compositions and in household care compositions in concentrations preferably ranging from 0.01 to 10% by weight relative to the total weight of the compositions, and more preferably from 0.05 and 2% by weight.

The conditioner and rheology modifier of the invention can be used in cosmetic compositions and in household care compositions for its viscosity-enhancing, stabilizing and conditioning properties, especially in the preparation of shampoos, hair conditioners, skin creams, personal or household care detergents and softeners.

Examples of cosmetic compositions according to the invention are body, hands and face creams, skin conditioners, hair gels and lotions (such as hair setting lotions, fixing and balms), hair colouring and bleaching creams, sunscreen compositions, cleansing, moisturizing and perspiring fluids, shampoos, two-in-one shampoos, perfumes, cleansing soaps and bars, and other products for similar applications.

The household care compositions of the invention include, but are not limited to: hard surface cleaning gels, bars, emulsions and liquid compositions, dry or damp dusting, cleaning and/or disinfecting wipes, fabric detergents and conditioners.

The conditioner and rheology modifier and the cationic galactomannan and xyloglucan of the present invention improves the deposition on hair and skin of the fatty ingredients of cosmetic compositions, such as oils, vitamins and emollients, and the persistence of their perfumes and fragrances, while providing effective conditioning and, if desired, thickening effect.

They are easily soluble in water, and their thickening effect is not impaired by the presence of surfactants, which are normally present in cosmetic and household care compositions.

The cosmetic compositions of the invention contain the usual ingredients, such as surfactants, moisturizers, emollients, sunscreens, hydrophilic or lipophilic active agents such as ceramides, anti-free-radical agents, insect repellents, skin coolants, deodorants, antiperspirant actives, hair treatment agents, oral care agents, slimming agents, bactericides, sequestering agents, antidandruff agents, antioxidants, preserving agents, basifying or acidifying agents, fragrances, fillers, dyestuffs, other polymers and emulsifiers, gelling agents, foaming agents.

Also, the household care compositions comprise the ingredients conventionally used in the fields, such as surfactants, emollients, insect repellents, bactericides, sequestering agents, antioxidants, preserving agents, basifying or acidifying agents, fragrances, fillers, dyestuffs, other polymers and emulsifiers, gelling agents, foaming agents, deodorizers, insecticides, cleaning agents, disinfectants, softeners, laundry detergents, dishwashing detergents.

The cosmetic compositions and the household care compositions of the invention usually also contain an acceptable liquid medium, which, according to the final use of the composition, is compatible with any keratin substance, such as skin, nails, hair, wool and the like.

The acceptable medium may represent from 5% to 98% of the total weight of the compositions. The typical acceptable medium is water.

Acceptable organic solvents may replace or partly substitute the water.

The organic solvents may be hydrophilic organic solvents, lipophilic organic solvents, amphiphilic solvents or mixtures thereof.

Examples of hydrophilic organic solvents are linear or branched lower monoalcohols having from 1 to 8 carbon atoms, such as ethanol, propanol, butanol, isopropanol and isobutanol; polyethylene glycols having from 6 to 80 ethylene oxides; polyols such as propylene glycol, butylene glycol, glycerol and sorbitol; mono- or dialkyl isosorbide in which the alkyl groups have from 1 to 5 carbon atoms, such as dimethyl isosorbide; glycol ethers such as diethylene glycol monomethyl or monoethyl ether and propylene glycol ethers such as dipropylene glycol methyl ether.

Among the utilisable amphiphilic organic solvents we cite polyols such as polypropylene glycol (PPG) derivatives, such as fatty acid esters of polypropylene glycol and fatty alcohol ethers of PPG.

Utilisable lipophilic organic solvents are, for example, fatty esters such as diisopropyl adipate, dioctyl adipate and alkyl benzoates.

The cosmetic compositions and the household care compositions of the present invention may be in the form of solution, emulsion, dispersion, gel, cream, paste, bar or wet wipe.

They may contain an oil, such as a mineral oil, a vegetable oil, an animal oil, a synthetic oil, silicone oils and mixture thereof.

Examples of utilizable oils are paraffins, liquid petroleum jelly, jojoba oil, coconut oil, sweet almond oil, olive oil, rapeseed oil, castor oil, sesame oil, avocado oil, groundnut oil, isoparaffins, amodimethicones, dimethiconols, cyclopentasiloxanes, and mixture thereof.

To better illustrate the invention, the following examples are reported to show the preparation of various conditioner and rheology modifier according to the invention and the effect of their addition in exemplary cosmetic compositions.

The examples are merely set forth for illustrative purposes all parts and percentages being by weight, unless otherwise indicated.

EXAMPLES

Example 1

(Comparative)

In a 5 liters stirred reactor, 800 g of guar powder were loaded at room temperature and the atmosphere was made inert by means of vacuum/nitrogen washings. 520 g of 1/2 water/isopropanol solution was added under vigorous stirring. After being stirred for 10 minutes, 201 g of an aqueous 30% wt sodium hydroxide solution were added and stirred for additional 15 minutes. 284 g of an aqueous 65% by weight solution of (3-chloro-2-hydroxypropyl)trimethyl ammonium chloride (QUAB 188) were added to the mixture, and heated to 50° C. for 2 hours. The reaction mass was then cooled to 40° C. and the pH was adjusted to about 5 with acetic acid. 40 g of glyoxal (40% in water) were added and the resulting mixture was stirred at 50° C. for 1 hour.

The product was purified by washing with water. Thus 200 g of reaction mixture were dispersed in 1400 g of tap water at pH below 7, left under stirring for few minutes, then filtered under vacuum on a fabric filter. The cationic guar on the filter was further washed with 300 g of tap water at pH below 7.

The cationic guar so obtained was dried on a fluid bed drier using hot air until the moisture content was about 3% by weight and then milled.

Example 2

In a 5 liters stirred reactor, 800 g of guar splits were loaded at room temperature and the atmosphere was made inert by means of vacuum/nitrogen washings. A mixture of 310 g of water and 180 g of an aqueous 30% wt sodium hydroxide solution was added under vigorous stirring. After being stirred for 30 minutes, 256 g of an aqueous 65% wt solution of (3-chloro-2-hydroxypropyl)trimethyl ammonium chloride (QUAB 188) were added and the mixture was heated to 50° C. for 2 hours. 180 g of the aqueous 30% wt sodium hydroxide solution were added again and the mixture was stirred at 50° C. for additional 2 hours. The reaction mass was then cooled to 40° C. and the pH was adjusted to about 5 with fumaric acid. 50 g of glyoxal (40% in water) dissolved in 80 g of water were added and the resulting mixture was stirred at 50° C. for 40 minutes. The cationic guar so obtained was dried on a fluid bed drier using hot air until the moisture content was about 3% by weight and then milled.

Example 3

In a 5 liters stirred reactor, 800 g of guar splits were loaded at room temperature and the atmosphere was made inert by means of vacuum/nitrogen washings. A mixture of 310 g of water and 180 g of an aqueous 30% wt sodium hydroxide solution was added under vigorous stirring. After being stirred for 30 minutes, 256 g of an aqueous 65% wt solution of QUAB 188 and 200 g of water were added and the mixture was heated to 50° C. for 2 hours. Other 60 g of an aqueous 30% wt sodium hydroxide solution were added to the mixture, which was then treated at 50° C. for 1 hour. The reaction mass was then cooled to 40° C. and the pH was adjusted to about 5 with acetic acid. 50 g of glyoxal (40% in water) dissolved in 80 g of water were added and the resulting mixture was stirred at 50° C. for 40 minutes. The cationic guar so obtained was dried on a fluid bed drier using hot air until the moisture content was about 3% by weight and then milled.

Examples 4

(Comparative)

In a 5 liters stirred reactor, 800 g of guar splits were loaded at room temperature and the atmosphere was made inert by means of vacuum/nitrogen washings. A mixture of 430 g of water and 240 g of an aqueous 30% wt sodium hydroxide solution was added under vigorous stirring. After being stirred for 30 minutes, 256 g of an aqueous 65% wt solution of QUAB 188 were added to the mixture, which was then treated at 50° C. for 2 hours. After the treatment the reaction mass was cooled to 40° C. and the pH was adjusted to about 5 with acetic acid. 50 g of glyoxal (40% in water) dissolved in 80 g of water were added and the resulting mixture was stirred at 50° C. for 40 minutes.

The cationic guar was dried on a fluid bed drier using hot air until the moisture content was about 3% by weight and then milled.

Example 5

In a 5 liters stirred reactor, 800 g of guar powder were loaded at room temperature and the atmosphere was made inert by means of vacuum/nitrogen washings. A mixture of 180 g of water and 220 g of isopropyl alcohol was added and stirred at room temperature for 10 minutes. Then 180 g of an aqueous 30% wt sodium hydroxide solution were added. After being stirred for 15 minutes, 256 g of an aqueous 65% wt solution of QUAB 188 were added to the mixture and the reaction mass heated to 50° C. for 2 hours. Then 180 g of aqueous 30% wt sodium hydroxide and 180 g of water were added and the basic treatment was continued at 50° C. for 1 hour. The mass was then cooled to 40° C. and the pH was adjusted to about 5 with fumaric acid. 36 g of glyoxal (40% in water) dissolved in 63 g of isopropyl alcohol were added and the resulting mixture was stirred at 50° C. for 40 minutes. The solvent was distilled off. The cationic guar was dried on a fluid bed drier using hot air until the moisture content was about 3% by weight and then milled.

Example 6

In a 5 liters stirred reactor, 800 g of guar powder were loaded at room temperature and the atmosphere was made inert by means of vacuum/nitrogen washings. A mixture of 245 g of an aqueous 30% wt sodium hydroxide solution and 314 g of isopropyl alcohol was added and homogenized at room temperature for 10 minutes. Then, 365 g of an aqueous 65% wt solution of QUAB 188 were added and the mixture was heated to 50° C. for 1 hour. The reaction mass was cooled down at 35° C. and a second portion of 245 g of 30% wt sodium hydroxide was added. The mixture was homogenized at the 35° C. for 10 minutes, then other 365 g of an aqueous 65% wt solution of QUAB 188 were added and reaction mass was maintained at 50° C. for 2 hours. The mass was then cooled to 40° C. and a third portion of 200 g of an aqueous 30% wt sodium hydroxide solution was added. After being stirred at 50° C. for 2 hours, the reaction mass was cooled to 40° C. and the pH was adjusted to about 5 with acetic acid. The solvent was distilled off. The cationic guar was dried on a fluid bed drier using hot air until the moisture content was about 3% by weight and then milled.

Example 7

800 g of guar powder were loaded in a 5 liters stirred reactor at room temperature. The reaction atmosphere was made inert by means of vacuum/nitrogen washings, and, under vigorous stirring, 171 g of a 50% aqueous solution of NaOH diluted with a water (100 g)/isopropanol (316 ml) mixture were added. The reactor was evacuated and refilled three times with nitrogen. Then 80 g of propylene oxide were slowly added and the reaction mixture was maintained for 45 min at 70-75° C. under stirring.

Afterwards the reaction mass was cooled down to 40° C., 470 g of an aqueous 65% wt solution of QUAB 188 were added and the mixture was heated to 50° C. for 2 hours. Then 171 g of 50% wt sodium hydroxide and 100 g of water were added and the reaction mass was maintained under stirring at 50° C. for 2 hours. The reaction mass was then cooled to 40° C. and the pH was adjusted to about 5 with acetic acid. 50 g of glyoxal (40% in water) dissolved in 79 g of isopropyl alcohol were added and the resulting mixture was stirred at 50° C. for 40 minutes. The solvent was distilled. The cationic hydroxypropyl guar so obtained was dried on a fluid bed drier using hot air and milled. At the end of the process the product had a moisture content of about 3% by weight.

Example 8

(Comparative)

In a 5 liters stirred reactor, 800 g of fenugreek powder (Fen) were loaded at room temperature and the atmosphere was made inert by means of vacuum/nitrogen washings. A mixture of 200 g of water and 320 g of isopropyl alcohol was added followed by 201 g of an aqueous 30% wt sodium hydroxide solution. After being stirred for 10 minutes at room temperature, 284 g of an aqueous 65% wt solution of QUAB 188 were added and the mixture was heated to 50° C. for 2 hours. The pH was adjusted to about 5 with acetic acid, 40 g of glyoxal (40% in water) dissolved in 60 g of isopropyl alcohol were added and the resulting mixture was stirred at 50° C. for 40 minutes. The solvent was distilled off. The cationic fenugreek was dried on a fluid bed drier using hot air until the moisture content was about 3% by weight and then milled.

Example 9

80 g of the cationic fenugreek prepared according to Example 8 were loaded into a 0.5 liters reactor. The atmosphere was made inert by means of vacuum/nitrogen washings and the powder was soaked with a mixture of 20 ml of water and 32 ml of isopropyl alcohol. After being stirred for 10 minutes, 20 g of an aqueous 30% wt sodium hydroxide solution were added and the resulting mixture was stirred for 1 hour at 50° C. The reaction mass was cooled to 40° C. and the pH was adjusted to about 7 with acetic acid. The solvent was distilled off. The cationic fenugreek was dried on a fluid bed drier using hot air until the moisture content was about 3% by weight and then milled.

Example 10

In a 5 liters stirred reactor, 800 g of deoiled tamarind kernel powder (Tam) were loaded at room temperature and the atmosphere was made inert by means of vacuum/nitrogen washings. A mixture of 100 g of water and 316 g of isopropyl alcohol was added and stirred for 10 minutes. Then 171 g of an aqueous 50% wt sodium hydroxide solution were sprayed on the mixture, which was then homogenized for 15 minutes. 396 g of an aqueous 65% wt solution of QUAB 188 were added and the mixture was heated to 50° C. for 2 hours. Other 171 g of an aqueous 50% wt sodium hydroxide solution were added and the basic treatment was continued at 50° C. for additional 2 hours. The reaction mass was then cooled to 40° C. and the pH was adjusted to about 5 with acetic acid. The solvent was distilled off and the cationic tamarind was dried on a fluid bed drier using hot air until the moisture content was about 3% by weight and then milled.

Example 11

In a 0.5 liters stirred reactor, 80 g of cassia powder (Cas) were loaded at room temperature and the atmosphere was made inert by means of vacuum/nitrogen washings. A mixture of 18 g of water and 22 g of isopropyl alcohol was added and stirred at room temperature for 10 minutes. 18 g of an aqueous 30% wt sodium hydroxide solution were added. After 15 minutes of homogenization, 26 g of an aqueous 65% wt solution of QUAB 188 were added and the mixture was heated to 50° C. for 2 hours. Then 18 g of 30% wt sodium hydroxide and 18 g of water were added and the reaction mass was stirred at 50° C. for 1 hour. The reaction mass was then cooled to 40° C. and the pH was adjusted to about 5 with acetic acid. The solvent was distilled off. The cationic cassia was dried on a fluid bed drier using hot air until the moisture content was about 3% by weight and then milled.

Example 12

In a 5 liters stirred reactor, 800 g of locust bean gum (Loc) powder were loaded at room temperature and the atmosphere was made inert by means of vacuum/nitrogen washings. A mixture of 210 g of an aqueous 50% wt sodium hydroxide solution and 316 g of isopropyl alcohol was added and stirred at room temperature for 10 minutes. Then, 485 g of an aqueous 65% wt of QUAB 188 solution were added and the mixture was heated to 50° C. for 1 hour. A second portion of 210 g of 50% wt sodium hydroxide was added and the mixture was homogenized for 10 minutes. Then other 485 g of an aqueous 65% wt solution of QUAB 188 were added and the mixture was again heated to 50° C. for 2 hours. A third portion of 210 g of aqueous 50% wt sodium hydroxide solution was added. After being stirred at 50° C. for 1 hour, the reaction mass was cooled to 40° C. and the pH was adjusted to about 5 with fumaric acid. The solvent was distilled off. The cationic locust bean gum so obtained was dried on a fluid bed drier using hot air until the moisture content was about 3% by weight and then milled.

$DS_{cat}$ and MS were determined by $^1$H-NMR analysis after purification from the reaction by-products by dialysis and lyophilization.

The RVT Brookfield® viscosity was determined on 1% wt solution in water at 20 rpm and 20° C.

The $DS_{cat}$, the MS, the RVT Brookfield® viscosity in mPa·s (VB), the content of Chlorohydrin and Glycol (% by weight) of the products of the Examples 1-14 are reported in Table 1.

The amount of NaOH used in step b) of the procedure (p/100p=parts by weight per 100 parts by weight of galactomannan or xyloglucan) and the length of time of the basic treatment of step b) are also reported in minutes (Time).

The results of Table 1 show that the procedure of the invention is able to reduce considerably the residual content of (3-chloro-2-hydroxypropyl)trimethyl ammonium chloride, down to <0.01% (<100 ppm), without affecting the rheological properties of the different polysaccharides.

TABLE 1

| Ex. | PS | $DS_{cat}$ | MS | NaOH p/100p | Time (minutes) | VB | Chlorohydrin % | Glycol % |
|---|---|---|---|---|---|---|---|---|
| 1* | Guar | 0.14 | — | — | — | 4750 | 0.13 | 0.35 |
| 2 | Guar | 0.14 | — | 6.75 | 120 | 1180 | <0.01 | 3.37 |
| 3 | Guar | 0.14 | — | 2.25 | 60 | 1315 | <0.01 | 4.16 |
| 4* | Guar | 0.12 | — | — | — | 1110 | 1.43 | 3.84 |
| 5 | Guar | 0.14 | — | 6.75 | 60 | 1820 | 0.03 | 2.92 |
| 6 | Guar | 0.44 | — | 7.5 | 120 | 267 | <0.01 | 5.69 |
| 7 | Guar | 0.28 | 0.32 | 10.7 | 120 | 520 | 0.09 | 3.66 |
| 8* | Fen | 0.14 | — | — | — | 284 | 3.69 | 2.75 |
| 9 | Fen | 0.14 | — | 7.5 | 60 | 40 | 0.13 | 3.15 |
| 10 | Tam | 0.29 | — | 10.7 | 120 | 85 | 0.07 | 3.66 |
| 11 | Cas | 0.14 | — | 6.75 | 60 | 13 | <0.01 | 4.01 |
| 12 | Loc | 0.40 | — | 13.1 | 60 | 18 | 0.05 | 3.08 |
| 13 | Guar | 0.14 | — | 6.75 | 120 | 1935 | <0.01 | 3.12 |
| 14 | Guar | 0.13 | — | 6.75 | 120 | 915 | <0.01 | 3.19 |

*Comparative
PS = galactomannan or xyloglucan

Example 13

A cationic guar was prepared by following the procedure of Example 2, except that no glyoxal was added and the pH was adjusted to about 10 with $CO_2$.

Example 14

A cationic guar was prepared by following the procedure of Example 2, except that no glyoxal was added.

Characterization of the Products of the Examples

The determination of the (3-chloro-2-hydroxypropyl) trimethyl ammonium chloride (Chlorohydrin) and (2,3-dihydroxypropyl)trimethyl ammonium chloride (Glycol) content was carried out by means of ion exchange chromatography. A DIONEX ICS 5000 DC ion chromatograph (Thermo Scientific) equipped with a conductimetric detector, an IonPac CG-14, 50×4.0 mm pre-column, and a IonPac CS-14, 250×4.0 mm column, was used. The eluent was a 95/5 water/0.1 M methanesulphonic acid solution at a flow of 1.0 ml/min. Different amount of sample, depending on the expected concentration, were weighed in 5.0 ml of methanol and vigorously stirred for 10 min. The sample solution were then centrifugated, separated and diluted 1:1 with water and injected in the chromatograph. A (3-chloro-2-hydroxypropyl)trimethyl ammonium chloride solution at known concentration was used as reference standard. The Glycol content was quantified using the same response factor of the Chlorohydrin.

Applicative Tests
Test 1

Six shampoos were prepared according to the formula reported in Table 2.

The cationic guar of Examples 2 and 5 were used as conditioning agents and compared with the cationic galactomannans of Example 1 and with the commonly used conditioners Ucare JR-30M and Merquat 550 (commercialized by Dow Chemical Company and Lubrizol Corp., respectively).

The shampoos were prepared adding the conditioning agent to water under vigorous stirring; adjusting the pH to 8-8.5 and, in order to assure the complete swelling of the polymer, stirring for about 20 minutes before adding the other ingredients.

TABLE 2

| INCI Name (or Function) | Parts by weight |
|---|---|
| Conditioner | 0.5 |
| Sodium Laureth Sulfate (27% active matter) | 30 |
| Cocamidopropyl Betaine (30% active matter) | 8 |
| Cocamide MEA (80% active matter) | 1.5 |
| Preservative | 0.2 |
| Citric acid (20% water solution) | to pH 5.5 |
| Aqua | to 100 |

In order to avoid harmful interaction between the cationic charge of polysaccharides and the anionic charge of primary surfactant, cocamidopropyl betaine was added before Sodium Laureth Sulfate.

The mixture was then heated to 60° C. before adding Cocamide MEA. After cooling down to 25° C., the preservative was added and, finally, the pH was adjusted to a value comprised between 5 and 5.5.

A control shampoo was prepared using the formula and procedure without the addition of any conditioner.

The RVT Brookfield viscosity (20 rpm@25° C.) of the different shampoos are reported in Table 3 together with the stability after three months at 25° C.

TABLE 3

| Example | Viscosity (mPa · s) | Stability (3 months 25° C.) |
|---|---|---|
| Control** | <100 | — |
| Example 1* | 2850 | No Separation |
| Example 2 | 7750 | No Separation |
| Example 5 | 1900 | No Separation |
| Ucare JR-30M* | 5200 | No Separation |
| Merquat 550* | 870 | No Separation |

*Comparative
**Without conditioner

The cationic polysaccharides of the invention (Examples 2 and 5) show thickening performances similar or better than the performances of cationic guar of the prior art, despite their lower thickening performance in water.

Test 2

Four skin cleansing compositions were prepared according to the formula reported in Table 4 and the following manufacturing procedure: add one by one the ingredients of phase A and heat till 70° C. In a separate vessel heat phase B.

The conditioner is dissolved under vigorous stirring in Glycerin.

Emulsify phase B into phase A, under continuous stirring cool down till 40° C. When the required temperature is reached, add phase C to the main vessel and stir until homogenous.

The final pH is around 5.8-6.0.

The cationic guars of Examples 13 and 14 were used as conditioners and compared with the cationic galactomannans of Example 1 and with a control formulation.

The RVT Brookfield viscosity (20 rpm@25° C.) of the different skin cleansing compositions are reported in Table 5 together with the stability after three months at 25° C.

TABLE 4

| | INCI | % |
|---|---|---|
| | Phase A | |
| 1 | Aqua | up to 100 |
| 2 | Tetrasodium EDTA | 0.02 |
| 3 | Sodium Laureth Sulfate, 30% a.m. | 33.4 |
| 4 | Cocamide MEA | 1 |
| 5 | Glycerin | 2.6 |
| 6 | Cocamidopropyl Betaine, 30% a.m. | 5 |
| | Phase B | |
| 1 | Petrolatum | 3 |
| 2 | Seed Oils | 18 |
| 3 | Lauric acid | 2 |
| 4 | Stearic acid | 2 |

TABLE 4-continued

| | INCI | % |
|---|---|---|
| | Phase C | |
| 1 | Conditioner | 0.6 |
| 2 | Glycerin | 2.4 |

TABLE 5

| Example | Viscosity (mPa · s) | Stability (3 months 25° C.) |
|---|---|---|
| Control** | <100 | Separation after 1 day |
| Example 1* | 8050 | No Separation |
| Example 13 | 7240 | No Separation |
| Example 14 | 8400 | No Separation |

*Comparative
**Without conditioner

The cationic guars of Example 13 and 14 show a good thickening performance despite their lower thickening performance in water.

Test 3

Wet Detangling

Four shampoos were prepared according to the formula reported in Table 6.

The shampoos were prepared adding the conditioner to water under vigorous stirring; adjusting the pH to 8-8.5 (not required for Example 13) and, to assure the complete swelling of the polymer, stirring for about 20 minutes before adding the other ingredients.

TABLE 6

| INCI name (or function) | Parts by weight |
|---|---|
| Conditioner | 0.5 |
| Sodium Laureth Sulfate (active matter 27%) | 37.5 |
| Cocamidopropyl Betaine (active matter 30%) | 12.7 |
| Pearlizing agent | 3 |
| Panthenol | 1 |
| Preservative | 0.2 |
| Citric acid (20% solution in water) | to pH 5.5 |
| Aqua | to 100 |

The Cocamidopropylbetaine was added before Sodium Laureth Sulfate and the mixture was heated to 60° C. After cooling, the remaining ingredients were added and the pH was adjusted to 5-5.5.

A control shampoo was prepared using the formula and procedure without the addition of any conditioner.

The RVT Brookfield viscosity (20 rpm at 25° C.) of the different shampoos are reported in Table 7.

Hairs, 25 cm long, bleached, European, assembled in swatches having a weight of 1 gram and a width of about 1.5 cm (Haarhaus Kerling, Germany) were used for the wet comb test.

The hair swatches were first cleansed by wetting with 37° C. running water for 60 seconds, washed for 60 seconds with 3.0 ml of the 10% Sodium Laureth Sulfate solution and then rinsed under 37° C. running water for 60 seconds. In a second step, each hair swatch was wetted under running water for 60 seconds and shampooed for 45 seconds by applying 0.5 gram of shampoo per gram of hair along the hair length and rinsed again under 37° C. running water for 60 seconds.

The shampooed hair swatches were then gently hand combed to remove major tangles and then combed for six times at 300 mm/min using a Dynamometer equipped with a fine tooth comb. Between each combing cycle, the hair was rewetted with water to keep it wet.

Combing force versus displacement curves were registered. The average combing force between interval 30 and 70 mm were calculated. From the 6 combing cycle values, the cycle average wet combing force was calculated for each hair swatch. 5 hair swatches were treated with each shampoo and used to determine the average combing force for the shampooed samples. The lower the value of the force, the higher the wet conditioning efficiency of the shampoo.

As reference the average combing force of 5 untreated hair swatches was determined.

The Combing Force Reduction (CFR %) was calculated according to the formula shown below:

$$CFR\% = \frac{ACFt - ACFu}{ACFu} \times 100$$

where
$ACF_t$=average combing force of the treated sample
$ACF_u$=average combing force of the untreated sample.
The results are reported in Table 7.

TABLE 7

|  | CFR % |
|---|---|
| Control** | −8 |
| Example 1* | −24 |
| Example 13 | −47 |
| Polyquaternium 10* | −37 |

*Comparative
**without conditioner

The conditioner of Example 13 has a much better conditioning effect than the purified comparative conditioner of Example 1 and the commercial conditioner Polyquaternium 10, that has cationic DS of about 0.3-0.6.

The invention claimed is:

1. A procedure for preparing a conditioner and rheology modifier comprising:
   i) from 60 to 90% by weight of a cationic galactomannan or a cationic xyloglucan, having a cationic degree of substitution of from about 0.01 to about 3;
   ii) from 1% to 10% by weight of (2,3-dihydroxypropyl) trimethyl ammonium chloride; and
   iii) less than 0.15% by weight of (3-chloro-2-hydroxypropyl)trimethyl ammonium chloride; comprising:
   a) reacting 100 parts by weight of galactomannan or xyloglucan with from 1 to 600 parts by weight of (3-chloro-2-hydroxypropyl)trimethyl ammonium chloride or of (3-epoxypropyl)trimethyl ammonium chloride with from 0.4 to 200 parts by weight of sodium hydroxide (or an equivalent amount of another alkaline hydroxide) in from 5 to 500 parts of water or of a water/alcohol mixture containing from 20 to less than 100% by weight of water;
   b) adding from 0.1 to 400 parts by weight of sodium hydroxide (or an equivalent amount of another alkaline hydroxide) to a mixture obtained from step a) and stirring for from 10 to 300 minutes, at a temperature of from 30° C. to 90° C.; and
   c) with no purification by washing with water or solvents, drying and milling a mixture obtained from step b);
   wherein the cationic galactomannan or cationic xyloglucan has a cationic degree of substitution of from about 0.05 to about 0.7 and the conditioner and rheology modifier has a residual concentration of (2,3-epoxypropyl)trimethyl ammonium chloride of less than 0.15% by weight.

2. The procedure of claim 1 wherein the pH of the mixture obtained from Step b) is corrected with an acid.

3. The procedure of claim 1 wherein the stirring in step b) is for from 60 to 150 minutes.

4. The procedure of claim 1 wherein the temperature in step b) is from 45° C. to 80° C.

5. The procedure of claim 1 wherein in step a) 100 parts by weight of galactomannan or xyloglucan are reacted with from 1 to 600 parts by weight of (3-chloro-2-hydroxypropyl) trimethyl ammonium chloride.

6. The procedure of claim 5 wherein in step b) from 2 to 90 parts by weight of sodium hydroxide (or equivalent amount of another alkaline hydroxide) are added.

* * * * *